(12) United States Patent
Dorwarth et al.

(10) Patent No.: US 7,705,603 B2
(45) Date of Patent: Apr. 27, 2010

(54) SENSOR DEVICE FOR CONDUCTIVITY MEASUREMENT AND METHOD FOR ITS OPERATION

(75) Inventors: Ralf Dorwarth, Oberderdingen (DE); Rainer Münzner, Oberderdingen (DE); Kay Schmidt, Oberderdingen (DE)

(73) Assignee: E.G.O. Elektro-Geraetebau GmbH, Oberderdingen (DE)

( * ) Notice: Subject to any disclaimer, the term of this patent is extended or adjusted under 35 U.S.C. 154(b) by 0 days.

(21) Appl. No.: 12/276,795

(22) Filed: Nov. 24, 2008

(65) Prior Publication Data
US 2009/0072835 A1 Mar. 19, 2009

Related U.S. Application Data

(63) Continuation of application No. PCT/EP2007/004350, filed on May 16, 2007.

(30) Foreign Application Priority Data
May 24, 2006 (DE) ............... 10 2006 025 622

(51) Int. Cl.
*G01N 27/02* (2006.01)
*G01R 31/26* (2006.01)
(52) U.S. Cl. .............. 324/448; 324/439; 324/719
(58) Field of Classification Search .............. 324/448, 324/439, 719, 722
See application file for complete search history.

(56) References Cited

U.S. PATENT DOCUMENTS

| | | | | |
|---|---|---|---|---|
| 3,701,006 A | * | 10/1972 | Volkel et al. | 324/442 |
| 3,939,408 A | * | 2/1976 | Brown | 324/444 |
| 3,992,662 A | * | 11/1976 | Koepnick et al. | 324/442 |
| 3,993,945 A | * | 11/1976 | Warmoth et al. | 324/449 |
| 4,082,666 A | | 4/1978 | Jones et al. | |
| 4,227,151 A | | 10/1980 | Ellis et al. | |
| 4,410,329 A | | 10/1983 | Blevins et al. | |
| 5,038,110 A | | 8/1991 | Braun et al. | |
| 5,315,847 A | * | 5/1994 | Takeda et al. | 68/12.02 |

(Continued)

FOREIGN PATENT DOCUMENTS

DE 43 11 064 A1 10/1994

(Continued)

OTHER PUBLICATIONS

Fainerman et al., Accurate Analysis of the Bubble Formation Process in Maximum Bubble Pressure Tensionmetry, Jan. 2004, vol. 75, No. 1, pp. 213-221, Review of Scientific Instruments.

(Continued)

*Primary Examiner*—Timothy J Dole
*Assistant Examiner*—Farhana Hoque
(74) *Attorney, Agent, or Firm*—Alston & Bird LLP

(57) ABSTRACT

A sensor device for insertion into a water channel in a washing machine is provided with two electrodes as sensors on a sensor carrier. These electrodes are in direct contact with the water through apertures. The electrodes are connected to a transformer on the sensor carrier directly and without any further components or couplings being required. The other side of the transformer is connected to an activating and evaluating means, in particular to a microprocessor positioned on the same carrier.

13 Claims, 1 Drawing Sheet

U.S. PATENT DOCUMENTS

| | | |
|---|---|---|
| 6,185,989 B1 | 2/2001 | Schulze |
| 6,960,871 B1 * | 11/2005 | Kumasaka et al. ......... 310/359 |
| 2006/0191496 A1 | 8/2006 | Muenzner et al. |

FOREIGN PATENT DOCUMENTS

| | | |
|---|---|---|
| DE | 19505541 | 8/1996 |
| DE | 197 55 291 | 5/1999 |
| DE | 199 33 631 A1 | 2/2001 |
| DE | 20318463 | 3/2004 |
| DE | 20 2004 007 261 | 9/2004 |
| DE | 20 2004 012 573 | 12/2004 |
| EP | 0760472 | 3/1997 |
| EP | 0 940 494 A1 | 9/1999 |
| EP | 1 464 948 | 10/2004 |
| EP | 1530041 | 5/2005 |
| WO | WO 9417954 | 8/1994 |

OTHER PUBLICATIONS

German Search Report for German Application No. 10 2005 007 870.2.

German Search Report from German Application No. 10 2006 025 622.0.

International Search Report from PCT/EP2006/001537, dated May 26, 2006.

International Search Report from PCT/EP2007/004350 dated Sep. 3, 2007.

* cited by examiner

SENSOR DEVICE FOR CONDUCTIVITY MEASUREMENT AND METHOD FOR ITS OPERATION

CROSS REFERENCE TO RELATED APPLICATIONS

This application is a continuation of PCT/EP2007/004350, filed May 16, 2007, which in turn claims priority to DE 10 2006 025 622.0, filed on May 24, 2006, the contents of both of which are incorporated by reference.

FIELD OF THE INVENTION

The invention relates to a sensor device for conductivity measurement and to a method for operating such a sensor device.

BACKGROUND OF THE INVENTION

It is known for example from US 2006/0191496 A1 to fit a sensor device for conductivity measurement to a heating device for a washing machine or dishwasher. Two sensory areas extend into the water for conductivity measurement and are contacted to the outside in simple manner by electrical terminals.

EP 940494 A1 discloses providing such a sensor device on a tumble dryer. Two electrodes are provided on a sensor module for conductivity measurement with conductance electronics for activation and with an optical coupler for transmitting the signals for evaluation. The conductance electronics is connected to the mains voltage by means of a transformer. In this way it is possible to isolate the sensor module from the remaining equipment via the transformer and optical coupler.

A problem addressed by the present invention is to provide an aforementioned sensor device and a method for operating such a sensor device making it possible to obviate the problems of the prior art and in particular provide a simple practicably usable sensor device which operates reliably.

BRIEF DESCRIPTION OF THE DRAWINGS

An embodiment of the invention is described hereinafter relative to the attached diagrammatic drawings, wherein.

DETAILED DESCRIPTION

Figure 1:
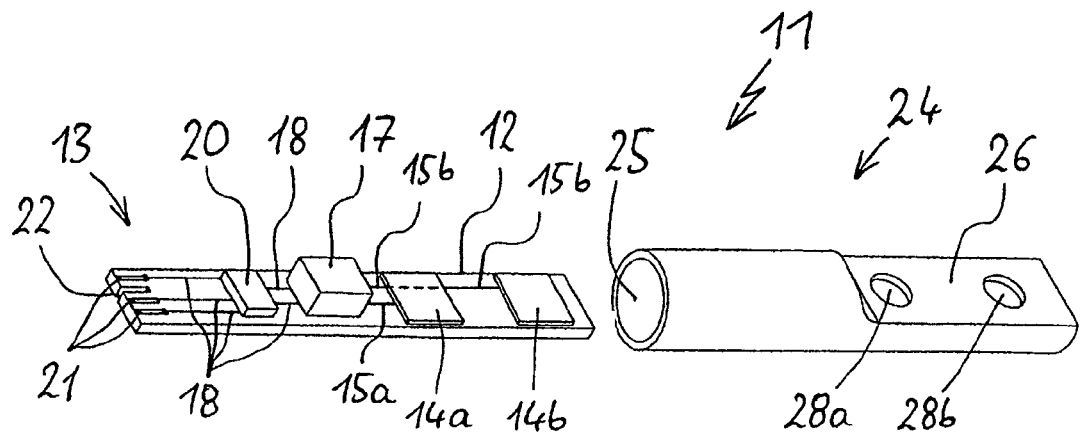
FIG. 1 illustrates an exploded view of sensor device with a carrier for the components and a sensor housing provided for the same.

This problem is solved by embodiments of a sensor device having the features and methods as claimed herein. Advantageous and preferred developments of the invention appear in the further claims and are explained in greater detail hereinafter. Some features of the invention are only explained once hereinafter, but independently of this apply to the different inventive constructions. By express reference the wording of the claims is made into part of the content of the description.

The water-containing electrical appliance or such an appliance operating with contaminated water, which can for example be a domestic electrical appliance such as a washing machine or dishwasher, is equipped with the sensor device. On a sensor carrier of the sensor device are provided two electrodes as sensors with which a conductivity measurement is performed. It is possible to determine the degree of contamination of the water from such a conductivity measurement. According to one embodiment of the invention the two electrodes or sensors are connected directly and without further components, coupling networks, etc. to a transformer. The situation can in particular be such that one terminal of the transformer is connected to one electrode and the other transformer terminal on said side is connected to the other electrode. This brings about an isolation of the electrodes, which necessarily must come into contact with the water, from the remaining electrical appliance, particularly an activating and evaluating means. Thus, isolation is implemented with limited constructional expenditure and, in particular, only those parts of the sensor device or appliance which must be live have to be isolated. As a result of the isolation directly at or very close to the electrodes, the energy to be transmitted is reduced. Thus, it is possible to reduce demands on the transformer with respect to size and therefore the overall size of the sensor device and also costs.

Advantageously, the transformer is located in the immediate vicinity of the electrodes. This, for example, involves a spacing roughly equivalent to that between the two electrodes and is typically a few centimeters, for example 1 cm to 5 cm or even up to 10 cm. As a result of such a small spacing, it is possible to reduce the overall size of the sensor device and also possible interference influences caused by unnecessarily long transmission paths, etc.

In another advantageous development of the invention, the electrodes and transformer form a common module or are components of the same. They can be placed on a common carrier, which can be a printed circuit board or the like. Electrical connections between the same, particularly between the transformer on the one hand and the electrodes on the other, are advantageously implemented as conducting tracks on the carrier. The carrier can either be made from plastic or a ceramic material. The fastening of the parts to the carrier can take place by adhesion or alternatively soldering. Such a module can easily be inserted in the sensor housing. It can be elongated, channel-like or tubular for housing the aforementioned module or components of the sensor device. In the assembled or ready-to-operate state the electrodes must at least partly be free or reachable. For this purpose, at least the transformer is located in the sensor housing interior. The electrodes are also advantageously placed in the sensor housing interior, for example, behind apertures in the sensor housing. These apertures are advantageously closed or sealed by the electrodes and in certain cases with the aid of specials sealants. It is also possible to fit the electrodes externally to the sensor housing, but then it is more difficult to implement the electrical connection with the transformer.

If the electrodes and transformer are placed in the sensor housing, advantageously, an electrical connection possibility is provided, which projects at a free or rear end from the sensor housing. This connection possibility can be a plug-in connection or exposed contact banks for soldering on.

In another embodiment of the invention, it is possible to provide a bus connection, particularly in an integrated circuit. With particular advantage, it forms part of the sensor device or is positioned within the sensor housing, for example between the transformer and the aforementioned connection possibility. Said connection possibility serves as an interface for activating and/or evaluating the sensors. Said bus connection permits a facilitated communication, i.e., the driving and evaluation of the electrodes. Moreover, as will be explained hereinafter, it allows the connection of further sensors. Thus, said bus connection should be positioned outside water-containing areas of the appliance in the same way as the aforementioned electrical connection.

Moreover, the sensor device, particularly in the sensor housing or on the aforementioned common carrier, can have an evaluation device, particularly a microprocessor, which can optionally have a few wiring components. Like the aforementioned bus connection, said microprocessor is placed on a different side of the transformer to the electrodes. It constitutes, so-to-speak, an incorporated intelligence of the sensor device. As a result, the measured data of the electrodes can be processed and preevaluated in order to obtain abstractly usable information. This can optionally be tapped on the outside via the bus connection, for example for use in a control unit of the electrical appliance. The advantage of information processing close to the electrodes or in the sensor device is that compared to a further transmission path, which may be exposed to interference influences, an easier, more detectable, clear signal can be received. Thus, the evaluation can, for example, incorporate a specific conductance or resistance indication, as well as the passing above or below of certain limit values.

It is possible to electrically insulate the aforementioned module of electrodes and transformer and in particular also with further devices such as the aforementioned microprocessor and/or bus connection and then solely the electrodes and optionally the electrical connection possibilities remain free. Such an electrical insulation can be constituted by a coating with an insulating layer, for example, insulating varnish or wax. After inserting the components or the module in the sensor housing, it is also possible to seal the same with one of the aforementioned insulating materials.

As has been intimated hereinbefore, it is possible to provide on the sensor device or on the sensor housing further sensors, which can also be exposed or reachable from the outside. This can be a temperature sensor for determining the temperature of the water. Further sensors are also possible, as will be described hereinafter. In one development a sensor or a further sensor can be so constructed such that it has a high-impedance at high frequencies, i.e., so-to-speak it is absent. In the case of low frequencies, it gives rise to a damping that can be evaluated, particularly on connection to the transformer. Particularly, if another sensor or the two electrodes for conductivity measurement are high-impedance at low frequencies and at high frequencies give rise to the damping that can be evaluated on the transformer, said several different types of sensors can be provided on the sensor device and can be simultaneously connected across the transformer or its two terminals on one side. As a function of the frequency range, one sensor or one sensor type is activated or evaluated. This obviously can be reversed with respect to the two aforementioned electrodes with frequency dependence.

In another development, it is possible for one or more sensors to in each case have a marked resonant frequency, at which they are then of much lower impedance than other frequencies in the remaining frequency range. Thus, virtually any number of sensors with in each case a different resonant frequency can be evaluated via the same transformer, namely by activation with its resonant frequency.

In yet another embodiment of the invention, at least one of the sensors is frequency independent. It is possible here that following on to the measurements at different frequencies, it is possible to measure the influence of the frequency-independent sensor, whose characteristics are known. It is possible in this way to eliminate its influences, so that once again the characteristics of the frequency-dependent sensors can be evaluated.

Thus, using the aforementioned method, it is possible in different ways to operate an inventive sensor device, particularly if with respect to the aforementioned electrodes, it has further sensors and they can be constructed according to one of the aforementioned examples.

These and further features can be gathered from the claims, description and drawings and the individual features, both singly or in the form of subcombinations, and can be implemented in an embodiment of the invention in other fields and can represent advantageous, independently protection constructions for which protection is claimed here. The subdivision of the application into individual sections and the subheadings in no way restrict the general validity of the statements made thereunder.

Turning now to the figures, FIG. 1 shows a sensor device 11 or its two parts. The elongated, for example plastic or ceramic carrier 12 has on its right-hand area the electrodes 14a and 14b, which have a spacing of a few centimeters and are constructed as conductive surfaces, as known from the aforementioned US 2006/0191496 A1. They are electrically connected to a transformer 17 via conducting tracks 15a and 15b on carrier 12. Like the electrodes 14, the transformer 17 is fixed to the carrier 12. It is constructed as a small transformer, as is known to one skilled in the art of signal technology.

By means of further conducting tracks 18, the transformer 17 is connected to a microprocessor 20, which is also fixed to the carrier 12. In turn the microprocessor 20 is connected or contactable by means of the conducting tracks 18 with contact banks 21 on the left-hand carrier end 13. As a function of the given construction, it is possible to have more than the shown three contact banks 21 or conducting tracks 18. In the case of a more complicated construction of carrier 12, it is also possible to have further contact banks on the underside of the carrier. Particularly with the slot 22 between them, the contact banks 21 are constructed for direct plugging in of a connector as the terminal.

The arrangement of the components and the conducting tracks on carrier 12 can possibly differ, as a function of the intended use and in particular the material or production of the carrier 12. The expert can select the most advantageous construction.

To the right in FIG. 1 can be seen the sensor housing 24. It is elongated and tubular, the left-hand end being open for the insertion of the carrier 12 using an opening 25, whereas the right-hand end is closed. Two apertures 28a and 28b are formed in the right-hand, flat part 26 of sensor housing 24. Reference is again made to US 2006/0191496 A1 in connection with the construction of said sensor housing 24.

Figure 2:
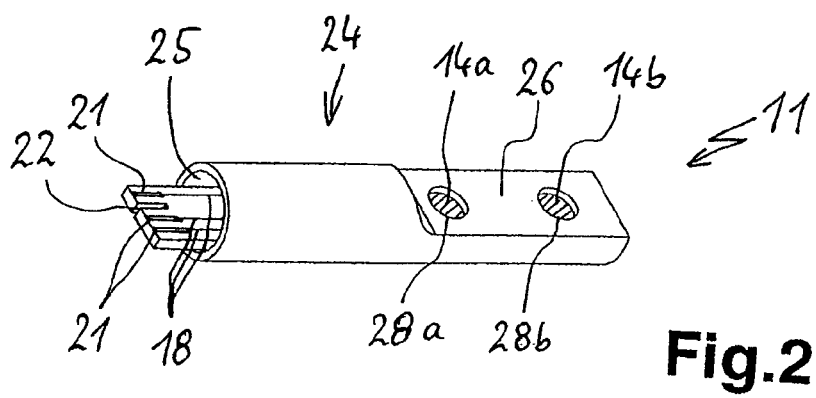
FIG. 2 illustrates the two parts plugged into one another from FIG. 1.

FIG. 2 shows how the carrier 12 is engaged in sensor housing 24. As is made clear by the hatching, the electrodes 14a and 14b are located beneath the apertures 28a and 28b. In particular, the electrodes 14 either seal the apertures 28 from the inside or use is made of sealants such as elastic sealing compounds, sealing rings or conductive sealing adhesives. The right-hand area of sensor housing 24 or sensor device 11, particularly the entire flat part 26, must project into a water duct.

Figure 3:
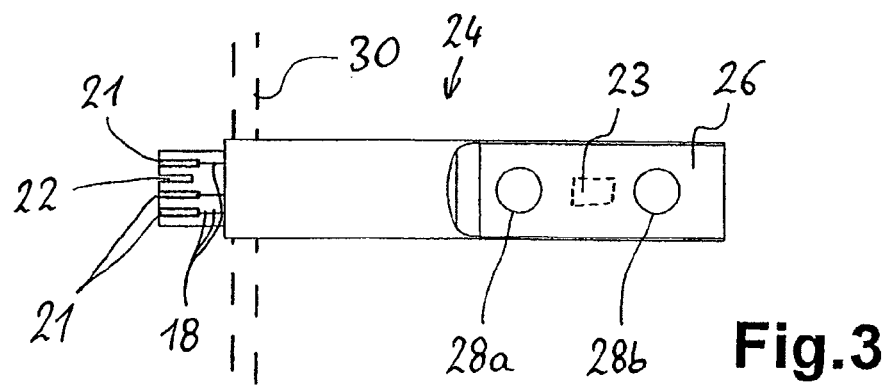
FIG. 3 illustrates a plan view of the sensor device according to FIG. 2 with a further temperature sensor, which is installed in the wall of a water duct of an electrical appliance.

This is illustrated in FIG. 3, where most of the area of the sensor device 11 passes through a wall 30 of a water duct or into the water in the latter. Fastening can take place in different ways, for example by bolting down, force fit or welding. It is also possible to firstly fix the sensor housing 24 to the wall 30 and then install the carrier 12.

FIG. 3 shows how the left-hand end with the opening 25 of sensor housing 24 projects out of the other side of the water duct 30, as does the left-hand carrier end 13 with the contact banks 21. This permits easy contacting and it is simultaneously ensured that no moisture can pass from the water duct to said areas.

As a variant in FIG. 3 and in broken line form is shown a temperature sensor 23, which is placed in the flat part 26 of sensor device 11. The temperature sensor 23 can be a conventional temperature sensor based on resistance or a temperature-dependent capacitance for frequency dependence. Like the electrodes 14 it is fastened to the carrier 12 and like said electrodes 14 can be connected via connecting tracks 15a and 15b to the two terminals of one side of transformer 17. It can have aforementioned frequency-dependent resistance characteristics, which permit a separate evaluation via the same transformer 17 as the conductivity measurement via electrodes 14. The temperature sensor 23 can either be in maximum thermal conducting contact with the sensor housing 24 or, like the electrodes 14, can be located at an aperture and can be in direct contact with water. However, it is advantageously located within the sensor housing 24 and is consequently encapsulated.

Activation and evaluation both of the conductivity measurement electrodes 14 and the temperature measurement temperature sensor 23 take place in the manner described hereinbefore, so that no further reference need be made thereto.

The temperature sensor can also be directly connected to the microprocessor 20. However, then there is no isolation and this should only take place if the temperature sensor 23 is located within the sensor housing 24.

The invention claimed is:

1. A sensor device for conductivity measurement for an electrical appliance having a water duct with contaminated water, wherein said sensor device has a sensor carrier, said sensor carrier having two electrodes as sensors for said conductivity measurement,
    wherein said two electrodes are connected directly without further components or further coupling circuits to a transformer configured to be connected to a control unit,
    wherein said transformer is positioned on said sensor carrier with a spacing from one of said two electrodes wherein said spacing is of the same order of magnitude as the spacing between said two electrodes,
    wherein said electrodes and said transformer form a common module on a common printed circuit board comprising electrical connections in the form of conducting tracks on said printed circuit board between said electrodes and said transformer, and
    wherein further sensors are provided on or in a sensor housing and are exposed to outside of said sensor housing.

2. The sensor device according to claim 1, wherein the transformer is positioned in said sensor device with a spacing of a few centimeters from said electrodes.

3. The sensor device according to claim 1, comprising an elongated or channel-like sensor housing wherein in the ready-to-operate state said electrodes are configured to be at least partly exposed to said contaminated water.

4. The sensor device according to claim 1, wherein an electrical connection is located that is configured to be outside water-contacting areas of said electrical appliance.

5. The sensor device according to claim 1, wherein on a common printed circuit board for said electrodes and said transformer, a microprocessor and its wiring is provided, wherein an electrical connection for said microprocessor is located outside a sensor housing of said sensor device.

6. The sensor device according to claim 1, wherein one said further sensor at high frequencies of an activation means has a high-impedance and at low frequencies has a low-impedance.

7. The sensor device according to claim 1, wherein one of said further sensors gives rise to a damping to be evaluated on said activation means or said transformer.

8. The sensor device according to claim 1, wherein at least one said sensors has a frequency dependency for activation and one other said sensor is frequency-independent for separately measuring values of said other sensor.

9. The sensor device according to claim 1, wherein at least one of said sensors has a resonant frequency for an evaluation of said sensor, wherein said at least one of said sensors has a lower impedance than other frequencies in a remaining frequency range.

10. A sensor device for conductivity measurement for an electrical appliance having a water duct with contaminated water, wherein said sensor device has a sensor carrier, said sensor carrier having two electrodes as sensors for said conductivity measurement,
    wherein said two electrodes are connected directly without further components or further coupling circuits to a transformer configured to be connected to a control unit, wherein said electrodes and said transformer are located in an interior of a sensor housing, and an electrical connection is provided at an end projecting from a rear of said sensor housing of a common printed circuit board for an electrical connection to said electrodes and said transformer and wherein further sensors are provided on or in said sensor housing and are exposed to outside of said sensor housing.

11. The sensor device according to claim 10, wherein said sensor housing has a tubular shape with one end comprising a flattened area and apertures therein and on which are located said electrodes.

12. The sensor device according to claim 11, wherein said electrodes are sealed against said apertures.

13. The sensor device according to claim 10, wherein a bus connection is provided between said transformer and said electrical connection as an interface for activating or evaluating said sensors.

* * * * *